US012594022B2

(12) United States Patent
Shepard et al.

(10) Patent No.: US 12,594,022 B2
(45) Date of Patent: Apr. 7, 2026

(54) INTEGRATED, FLEXIBLE, IMPLANTABLE, OPTICAL NEURAL INTERROGATION APPARATUS, COMPUTER-ACCESSIBLE MEDIUM, SYSTEM, AND METHOD FOR USE AND IMPLEMENTATION THEREOF

(71) Applicant: The Trustees of Columbia University in the City of New York, New York, NY (US)

(72) Inventors: Kenneth L. Shepard, Ossining, NY (US); Sajjad Moazeni, New York, NY (US); Eric Pollmann, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 663 days.

(21) Appl. No.: 17/582,375

(22) Filed: Jan. 24, 2022

(65) Prior Publication Data

US 2022/0218265 A1 Jul. 14, 2022

Related U.S. Application Data

(63) Continuation of application No. PCT/US2020/043336, filed on Jul. 23, 2020.

(60) Provisional application No. 62/878,050, filed on Jul. 24, 2019.

(51) Int. Cl.
| | |
|---|---|
| *A61B 5/00* | (2006.01) |
| *H10F 55/255* | (2025.01) |
| *H10F 77/169* | (2025.01) |

(52) U.S. Cl.
CPC .......... *A61B 5/4064* (2013.01); *A61B 5/0071* (2013.01); *A61B 5/0084* (2013.01); *H10F 55/255* (2025.01); *H10F 77/1698* (2025.01)

(58) Field of Classification Search
CPC .................................................. A61B 5/4064
See application file for complete search history.

(56) References Cited

U.S. PATENT DOCUMENTS

2012/0157804 A1* 6/2012 Rogers ................... H01L 24/86
                                              604/20

FOREIGN PATENT DOCUMENTS

WO      2019018020 A1      1/2019

OTHER PUBLICATIONS

Mitra, CMOS circuits for biological sensing and processing, Springer publications, 2018.*

(Continued)

*Primary Examiner* — Joseph M Santos Rodriguez
(74) *Attorney, Agent, or Firm* — Hunton Andrews Kurth LLP

(57) ABSTRACT

Exemplary embodiments of the present disclosure provide for an integrated, flexible, implantable, optical neural interrogation apparatus, computer-accessible medium, system, and method for use thereof. An integrated, flexible, fully-implantable, all-optical neural interrogation apparatus can include, e.g., a 2-dimensional (2D) planar array of optical photodetectors on an integrated electronic chip, the integrated electronic chip including control logic and image-capturing electronic circuitry, an amplitude or phase optical imaging mask for imaging, and a biocompatible packaging.

21 Claims, 9 Drawing Sheets

(56)                    References Cited

OTHER PUBLICATIONS

A wireless head mountable device with tapered optical fiber coupled laser diode for light delivery in deep brain regions, IEE transactions on biomedical engineering vol. 66, No. 7, Nov. 19, 2018 (Year: 2018).*

Emiliani, V. et al. (2015). All-Optical Interrogation of Neural Circuits. The Journal of Neuroscience, 35(41), 13917 LP-13926.

Hochbaum, D. R., et al. (2014). All-optical electrophysiology in mammalian neurons using engineered microbial hodopsins. Nature Methods, 11, 825.

Zhang, Z., et al. (2018). Closed-loop all-optical interrogation of neural circuits in vivo. Nature Methods, 15(12), 1037-1040.

Ghosh, K. et al. (2011). Miniaturized integration of a fluorescence microscope. Nature Methods, 8, 871.

Scott, B. et al. (2018). Imaging Cortical Dynamics in GCaMP Transgenic Rats with a Head-Mounted Widefield Macroscope. Neuron, 100(5), 1045-1058.e5.

Stamatakis, A. M., et al. (2018). Simultaneous Optogenetics and Cellular Resolution Calcium Imaging During Active Behavior Using a Miniaturized Microscope. Frontiers in Neuroscience, 12, 496.

Sawinski, J., et al. (2009). Visually evoked activity in cortical cells imaged in freely moving animals. Proceedings of the National Academy of Sciences, 106(46), 19557 LP-19562.

Zong, W., et al. (2017). Fast high-resolution miniature two-photon microscopy for brain imaging in freely behaving mice. Nature Methods, 14, 713.

Lee, C., et al. (2019). A 512-Pixel 3kHz-Frame-Rate Dual-Shank Lensless Filterless Single-Photon-Avalanche-Diode CMOS Neural Imaging Probe. IEEE International Solid-State Circuits Conference, ISSCC 2019, San Francisco, CA, USA, Feb. 17-21, 2019, 198-200.

Rae, B. R. et al. (2009). A CMOS Time-Resolved Fluorescence Lifetime Analysis Micro-System. Sensors, 9(11), 9255-9274.

Adams, J. K., et al. (2017). Single-frame 3D fluorescence micros-copy with ultraminiature lensless FlatScope. Science Advances, 3(12), e1701548.

Yona, G., Meitav, N., Kahn, I., & Shoham, S. (2016). Realistic Numerical and Analytical Modeling of Light Scattering in Brain Tissue for Optogenetic Applications. ENeuro, 3(1).

Gupta, S., Navaraj, W. T., Lorenzelli, L., & Dahiya, R. (2018). Ultra-thin chips for high-performance flexible electronics. Npj Flexible Electronics, 2(1), 8.

Kim, S., P. Tathireddy, R.A. Normann, and F. Solzbacher, Thermal Impact of an Active 3-D Microelectrode Array Implanted in the Brain.IEEE Transactions on Neural Systems and Rehabilitation Engineering, 2007. 15(4): p. 493-501.

Mirbozorgi, S.A., H. Bahrami, M. Sawan, L.A. Rusch, and B. Gosselin, A Single-Chip Full-Duplex High Speed Transceiver for Multi-Site Stimulating and Recording Neural Implants.IEEE Transactions on Biomedical Circuits and Systems, 2016. 10(3): p. 643-653.

International Search Report and Written Opinion for International Patent Application No. PCT/US2020/043336 mailed on Nov. 6, 2020.

Lee, C et al. "A 72×60 Angle-Sensitive SPAD Imaging Array for Lens-less FLIM"; Sep. 2, 2016 (Sep. 2, 2016) retrieved Sep. 30, 2020 (Sep. 30, 2020)]. Retrieved from the Internet: <URL: https:llwww.ncbi.nlm.nih.gov/pmc/articles/PMC5038700/>; Sensors (Basel); abstract, p. 1, last paragraph, p. 2, second paragraph, p. 3, second, third and last paragraphs, p. 4, second paragraph, p. 5, first paragraph, p. 9, third paragraph, p. 10, first paragraph, p. 15, second paragraph, p. 18, last paragraph.

Steude, A et al. "Arrays of microscopic organic LEDs for high-resolution optogenetics"; May 6, 2016 (May 6, 2016) [retrieved Oct. 1, 2020 (Oct. 1, 2020)]. Retrieved from the Internet: <URL: https:l/advances.sciencemag.org/content/2/5/e1600061 >; Science Advances; abstract, p. 1, first column, last paragraph, second column, last paragraph, p. 3, first column, first, second and third paragraphs, p. 5, second column, p. 6, first column, second column, last paragraph, p. 7, first column, third paragraph.

Bruschini, C et al. "Single-photon SPAD imagers in biophotonics: Review and Outlook"; Mar. 18, 2019 (Mar. 18, 2019)(re trieved Oct. 1, 2020 (Oct. 1, 2020)]. Retrieved from the Internet: <URL: https:l/arxiv.org/abs/1903.07351>; figure 3, p. 9, third and sixth paragraphs.

Karami, Met al. "Neural Imaging Using Single-Photon Avalanche Diodes"; Jan. 2017 [retrieved Sep. 30, 2020 (Sep. 30, 2020)]. Retrieved from the Internet: <URL: https://www.ncbi.nlm.nih.gov/pmc/articles/PMC5396169/>; Basic and Clinical Neuroscience; see entire document.

* cited by examiner

156

166

164

158

162

160

156

600

INTEGRATED, FLEXIBLE, IMPLANTABLE, OPTICAL NEURAL INTERROGATION APPARATUS, COMPUTER-ACCESSIBLE MEDIUM, SYSTEM, AND METHOD FOR USE AND IMPLEMENTATION THEREOF

CROSS-REFERENCE TO RELATED APPLICATION(S)

This application is a continuation of International Patent Application No. PCT/US2020/043336, filed on Jul. 23, 2020 that published as International Patent Publication No. WO 2021/016485 on Jan. 28, 2021, and also relates to and claims priority from U.S. Provisional Patent Application Ser. No. 62/878,050, filed on Jul. 24, 2019, the entire disclosures of which are incorporated herein by reference.

STATEMENT REGARDING FEDERALLY SPONSORED RESEARCH

This invention was made with government support under NS090596 awarded by the National Institutes of Health and N66001-17-C-4012 awarded by DOD/DARPA. The government has certain rights in the invention.

FIELD OF THE DISCLOSURE

The present disclosure relates generally to neural interrogation, and more specifically, to exemplary embodiments of an exemplary integrated, flexible, fully-implantable, all-optical neural interrogation apparatus, computer-accessible medium, system, and method for use and implementation thereof.

BACKGROUND INFORMATION

Understanding the human brain is one of the greatest scientific challenges. Despite many efforts in the field of neuroscience during the last few decades, there is still very little understanding of neural connectivity and the role of each neuron in brain computations and information processing. Optical functional imaging of the brain and optogenetics are among the current solutions to decipher the human brain. They enable localization of neurons in anatomical space and cell-type specificity via genetically encoded fluorescent markers. Combining both fluorescence imaging and optogenetics in a single device can enable all-optical neural interrogation. Such a device should be realized in a compact (e.g., small volume and weight) and minimally-invasive form factor while covering relatively large cortical areas and enabling free-behaving animal studies. In this regard, a variety of head-mounted "miniscopes" that include fluorescence imaging and optogenetics have been presented as a step towards achieving such an optical device. Most of these systems rely on wide-field fluorescence imaging, while two-photon miniscopes have been also realized. However, despite these efforts to miniaturize the conventional optical systems, the inherent trade-off between the field of view ("FoV") and the size (e.g., weight/volume) of the device limits their FoV to mm²-ranges. Additionally, using multiple of these miniscopes is not feasible due to their large packaging as well as the footprint of the head-mounting structure. Further, many of these miniscopes capable of optogenetics stimulation use wide-field excitation lacking the spatial selectivity essential for neural circuit studies over large FoVs.

Thus, it may be beneficial to provide an exemplary integrated, flexible, fully-implantable, all-optical neural interrogation apparatus, computer-accessible medium, system, and method for use thereof, which can overcome at least some of the deficiencies described herein above.

SUMMARY OF EXEMPLARY EMBODIMENTS

An exemplary integrated, flexible, fully-implantable, all-optical neural interrogation apparatus, computer-accessible medium, system, and method can include a 2-dimensional ("2D") planar array of optical photodetectors on an integrated electronic chip, the integrated electronic chip including control logic and image-capturing electronic circuitry, an amplitude or phase optical imaging mask for imaging, and a biocompatible packaging.

In some exemplary embodiments of the present disclosure, the tissue can be nervous tissue or living brain tissue. Further, neuronal activity can imaged based on at least one optical reporter, wherein the at least one optical reporter includes at least one of a genetically-encoded Calcium or voltage-dependent fluorescent protein, a bioluminescence protein, a chemical fluorescent reporter, or a fluorescent nanoparticle reporter. Further, the imaging can be lens-less and can be based on computational imaging algorithms. Further, an imager surface can be flexible and conformable to a tissue surface and curvature. Further, the integrated electronic chip can be a single complementary-metal-oxide-semiconductor ("CMOS") chip. In addition, the CMOS chip can be die-thinned so as to be flexible and pliable. Further, the biocompatible packaging includes a thickness of 500 micrometer or less.

According to an exemplary embodiment of the present disclosure, the exemplary apparatus can be (i) conformable to a tissue surface and curvature and (ii) sticks to the tissue surface to minimize implant dislocations. Further, the optical photodetectors can be single-photon avalanche photodiodes ("SPADs"), wherein the arrays of the SPADS can be time-gated. Further, the imaging field of view can be about 0.25 cm² or larger. Further, the exemplary apparatus can include a weight of less than 5 grams. Further, 3D volumes can be imaged using computational imaging procedures. According to additional exemplary embodiments of the present disclosure, the exemplary apparatus can further comprise light emitting diodes ("LEDs") for the fluorescence excitation of the tissue. Further, a set of the LEDs can be used to optogenetically stimulate cortical regions in a brain. Tissue cells can be labeled with cell-specific Opsins to enable optogenetics stimulation. Additionally or alternatively, a 2D LED array can perform optogenetics stimulation with spatial selectivity and programmable patterns. Electrical power and/or data in and out of the implant can be wirelessly transmitted to an external relay station.

According to further exemplary embodiments of the present disclosure, the exemplary apparatus, computer-accessible medium and method can facilitate cellular fluorescence imaging (e.g., resolution of <30 um) over large FoV (e.g., approximately cm²) in 3D cortical voxels (e.g., greater than 250 um deep) for the first time by exploiting a computational imaging procedure that eliminates the need of conventional optical components in an ultra-thin, conformable form factor. The exemplary apparatus can include an enhanced application specific integrated circuit ("ASIC") chip. This chip can contain (i) monolithic SPADs for high-quality imaging and (ii) 3D integrated LEDs as light sources. Further, the exemplary apparatus can include a wireless communication interface for wireless communication with outside systems, as well as a wireless power interface for charging the exemplary apparatus wirelessly.

Overall, according to further exemplary embodiments of the present disclosure, the exemplary apparatus, computer-accessible medium, and method can facilitate the following exemplary capabilities simultaneously: (i) cellular calcium/voltage fluorescence 3D imaging over a large FoV (e.g., $cm^2$-range), (ii) optogenetics using a 2D array of micro-LEDs, (iii) compact and conformable form-factor, and/or (iv) wireless power and data telemetry. With regard to cellular calcium/voltage fluorescence 3D imaging over a large FoV (e.g., $cm^2$-range), the FoV of the exemplary apparatus can be nearly equal to the size of the sensor, which can be over 1 $cm^2$. This can be advantageous compared with conventional imagers, where FoV can be set by the numerical aperture ("NA") of the lensing component and NA can be proportionate to the size of the lens. Thus, traditional imaging systems with larger FoV are expected to be larger and bulkier. Moreover, with the exemplary apparatus, computer-accessible medium and method, the target cortical area can be imaged in 3D, where the images can be resolved from multiple focal planes after processing the captured sensor data. According to an exemplary embodiment of the present disclosure, the imaging depth can depend on the excitation light penetration as well as the required signal-to-noise ("SNR") ratio.

With respect to the optogenetics using a 2D array of micro-LEDS, the exemplary apparatus, computer-accessible medium, and method can selectively optogenetically stimulate different regions of the FoV. An array of micro-LEDs, which can be flip-chip bonded to a CMOS chip, can be deployed to enable the control over the whole FoV in 2D with sub-mm2 resolution. Further, using light propagation simulations, it can be demonstrated that the stimulation can occur up to 700 um deep in the cortical tissue. With regard to the compact and conformable form factor, by exploiting time-gating and computational imaging procedures, the exemplary apparatus can be realized in a surface that can be thinner than 500 um and lighter than 2 g. According to an exemplary embodiment of the present disclosure, this can dramatically reduce the brain tissue immune response towards the implant and make the exemplary apparatus available for chronic applications. Additionally, implanting the exemplary apparatus can be easier as it can be slid into the brain using simple craniotomy steps. Further, larger brain areas can be interrogated by tiling multiple of these exemplary devices, which may not be possible for head-mounted miniscopes due to their bulky packaging.

With regard to the wireless power and data telemetry, the exemplary apparatus can be wirelessly powered as well as transmit captured imaging data to an external relay station. Further, the exemplary apparatus' setting and simulation patterns can be configured via a wireless link as well. According to an exemplary embodiment of the present disclosure, an ASIC chip can accommodate both a coil and wide-band antenna for these purposes. The tetherless aspect of the exemplary device opens up new degrees of freedom for neuroscientists to perform various behavioral experiments on freely-behaving animals. Further, the total power consumption for the implanted device can be below 45 mW, which can guarantee that the temperature of the brain tissue would not be increased by more than 1.5° C.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figures showing illustrative embodiments of the present disclosure, in which.

Figure 1A:
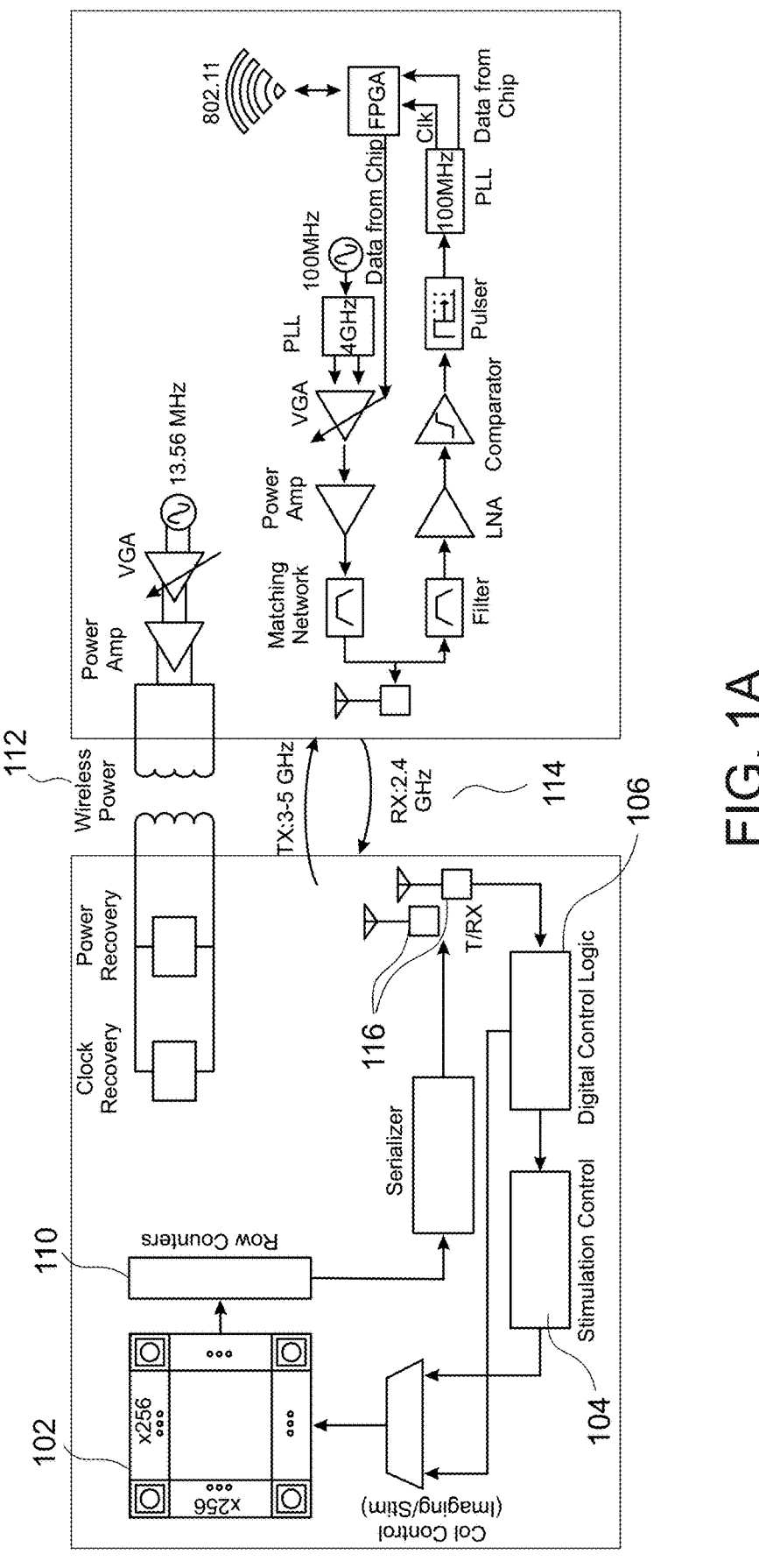
FIG. 1A is an exemplary block and schematic diagram of the exemplary apparatus including an image sensor array, control and logic circuitry, and wireless power and data transfer blocks according to an exemplary of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

FIG. 1A illustrates an exemplary block and schematic diagram of the exemplary apparatus according to an exemplary embodiment of the present disclosure that includes an image sensor array 102, a stimulation control arrangement/apparatus 104, a logic circuitry 106, a serializer 108, flow counters 110, wireless power blocks 112, and wireless data transfer blocks 114, according to an exemplary of the present disclosure. The exemplary apparatus can include an ASIC chip with fully-integrated single-photon avalanche photo-diodes ("SPADs") (e.g., which can be fabricated in a CMOS foundry) along with three-dimensional ("3D") integrated micro-LEDs as light sources. For example, the exemplary apparatus can include 160×160 SPAD-based imaging pixels with two separate arrays of 5×5 blue and green micro-LEDs for imaging illumination and optogenetics, which can achieve a 5×5 mm² Field of view ("FoV"), and can have an imaging resolution of about 30 um.

Additionally, the exemplary apparatus can include computational and time-gated fluorescence imaging methods, thereby eliminating the need for bulky optical lenses and filters conventionally used for optical functional imaging. For example, time-gating can be achieved by placing an active quenching circuit ("AQC") right next to each SPAD to reset/activate the detector right after the excitation light pulse can be passed. Further, an exemplary rolling-shutter procedure can be used to alleviate the dynamic power dissipation required for resetting the SPADs, and lower the required data-rate for the uplink. The FoV can still be imaged at sufficiently high frame-rates of 250 fps for 20 MHz laser excitation rates. Further, depending on the achieved SNR in the tissue, e.g., 8 times averaging can be achieved, while still capturing more than 30 fps to measure either calcium or voltage activity. The exemplary imaging resolution can be based on the pixel pitch, which can be 30 um.

According to an exemplary embodiment of the present disclosure, micro-LEDs can be 3D flip-chip bonded to the pads on the ASIC chip using Au-balls. An exemplary set of 5×5 arrays (e.g., blue LEDs) can be used for fluorescence imaging illumination. For example, neuronal activity can be imaged using genetically encoded Calcium indicators (e.g., GCamp6f) and/or other optical reporters. Further, due to a small parasitic capacitance associated with 3D bonding, illumination LEDs can generate short light pulses with fast falling edges, thereby facilitating time-gated fluorescence imaging. The programmable illumination pattern can be synchronized with the rolling-shutter imager to only illuminate the regions where the sensor columns can be active in order to reduce the background noise and alleviate photobleaching.

According to an exemplary embodiment of the present disclosure, the second set of micro-LEDs can be green LEDs, which can activate C1V1 opsins to stimulate the neurons optogenetically. The stimulation pattern, duration, and repetition rate can be configured using the stimulation control arrangement/apparatus 104. Layers of brain as deep as 700 um from the brain surface can be stimulated. Further, the isotropic emission pattern of LEDs can facilitate the whole FoV region to be covered with, e.g., a 5×5 array. Due to the slow repetition rate of optogenetic stimulation (e.g., 1-40 Hz), a time-multiplexed activation pattern can be deployed per column to reduce the maximum current drawn by the device, and to reduce the required decoupling capacitors. Further, decoupling capacitors can be embedded on the edges of the flexible package (e.g., off-chip) due to their required large capacity (e.g., approximatelyluF). With regard to the impact of missing sensor pixels due to the placement of micro-LEDs on the chip, because the exemplary apparatus, computer-accessible medium, and method can implement a computational imaging procedure, the image quality and resolution can be recovered by interpolating over the missing pixels. Thus, the exemplary placement of micro-LEDs in between imager pixels can have a negligible impact on the image quality.

According to an exemplary embodiment of the present disclosure, to facilitate the device to be fully implantable, a multi-antenna solution can be fully integrated onto the flexible CMOS chip as well. A power link 112 and a data link 114 can operate over two decades apart in frequency to avoid interference. For example, one set of antennas can operate to receive power at a lower carrier frequency (e.g., about 13.56

MHz). Specifically, e.g., an ISM band can be used at about 13.56 MHz with a coil that completely surrounds the outer circumference of the integrated circuit. Series resistance in the receiving coils can be reduced through the use of thick, wide metal to limit losses. As such, a battery s is not required to be incorporated into the implanted device. Simultaneously, another set of antennas 116 can be used to transmit and receive digital information using an ultra-wide band link at a center frequency of 4 GHz. For high rate data transfer off the chip, ultra-wide-band ("UWB") procedures can be used. Impulse radio ("IR") UWB has the benefit of a simple, digital-circuit-style, implementation. The exemplary IR-UWB system can be centered at about 4 GHz with a 900 MHz bandwidth (e.g., 3.1 GHz to 4.9 GHz). This exemplary bandwidth can facilitate the use of about 1.1 ns transmission pulses with 10 ns of reset time before the next pulse. The exemplary apparatus, computer-accessible medium, and method can support 100 Mb/s and 50 Mb/s uplink and downlink data-rates, respectively. Other uplink and down-link data rates (e.g., higher or lower) can also be supported. Down-link data can be used to program the device to boot-up and activate or configure the stimulation pattern for optogenetics.

Figures 1B, 1C:
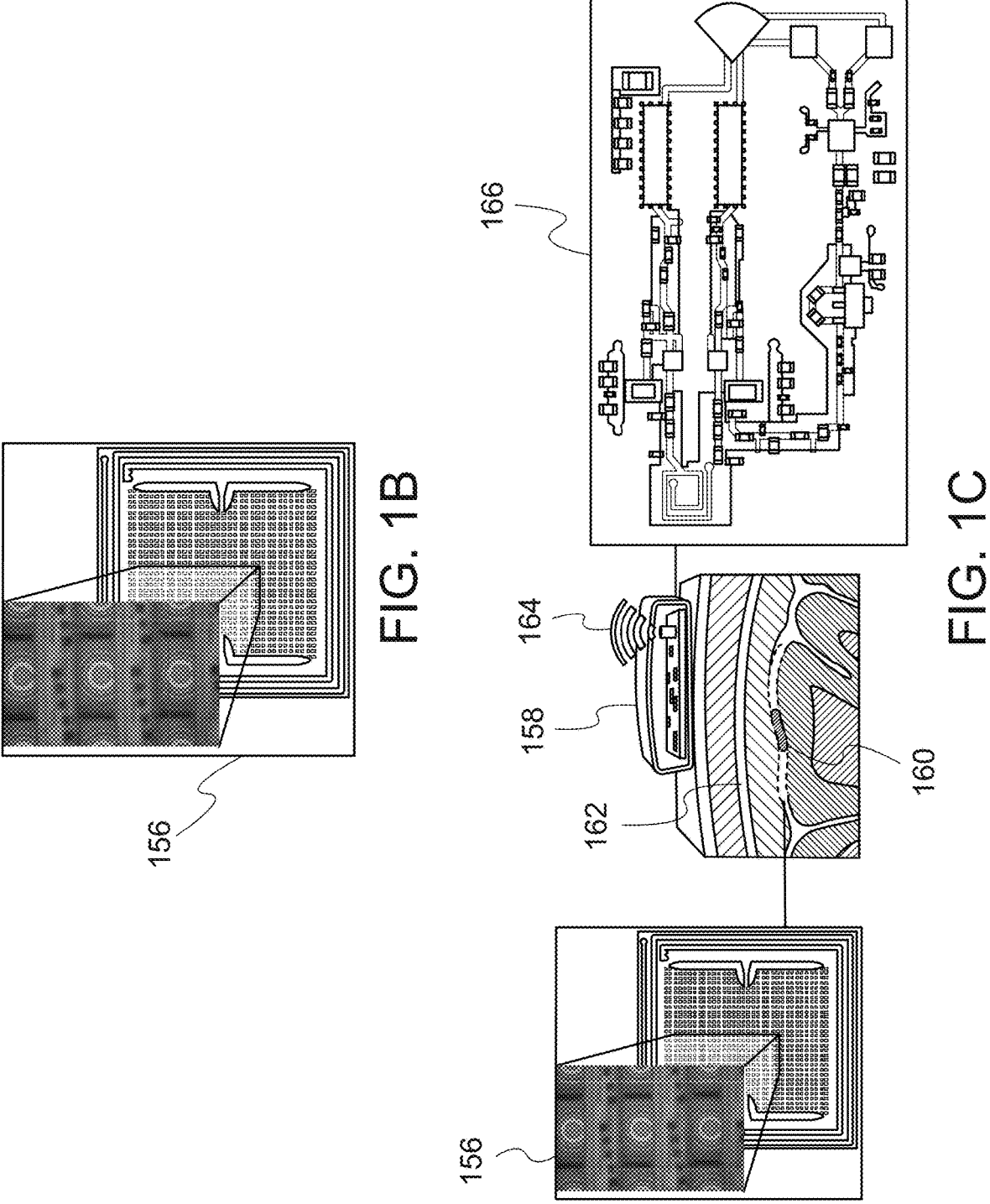
FIG. 1B is an exemplary micrograph of a SPAD-based sensory array according to an exemplary of the present disclosure.
FIG. 1C is a diagram of an exemplary external relay station according to an exemplary of the present disclosure.

FIG. 1B illustrates an exemplary micrograph 156 of a SPAD-based sensory array according to an exemplary of the present disclosure. In particular, FIG. 1B shows a micrograph 156 of previously-fabricated SPAD-based sensor array.

FIG. 1C shows an illustration of an exemplary external relay station 158 according to an exemplary of the present disclosure. For example, to provide power and to relay information between the implant 160 and a "base station" (e.g., a computer or smartphone), a battery-operated (e.g., 3.7-V, 4.2-Amp-hour lithium-ion battery, which can consume approximately 15 W when active and about 50 mW in standby and can give about 1 hour of activity on a battery charge) external relay station 158 can be positioned outside of the skull 162 of the patient, directly over the implant 160 within the brain. The external relay station 158 can serve as the power source for the device 160, as well as to relay data from the implanted chip through an industry-standard 802.11 wireless link 164. Additionally, the external relay station 158 can be configured to program and control the implanted device 160. This can include, e.g., selecting the optogenetics pattern as well as reading out the imaged data. The data can then be relayed to the base station for data processing and analysis. The exemplary external relay station 158 can be configured for mounting in a wearable form-factor (e.g., on a cap) that can interface with an external wireless camera, in addition to an external computing device. Further, the link between the external relay station 158 and other 802.11n wireless devices can be secured using any suitable standard (e.g., the WPA2 standard). The link between the external relay station 158 and the implant 160 can be secured with secret keys, if desired or necessary.

As shown in FIG. 1C, Relay station board 166 can include various exemplary modules that can be used to communicate with the implanted device and transfer the power wirelessly. The exemplary power transfer modules can include (i) on-board antennas, (ii) power amplifiers, (iii) a mixer, and (iv) signal generators. Additionally, various exemplary communication modules can be included that can be used to communicate with the control PC/phone via any suitable wireless communication protocol/standard (e.g., 802.11b, 802.11g, 802. ac, etc.) The communication modules can include one or more transceivers and one or more field programmable gate arrays to interface to power transfer modules.

Figure 1D:
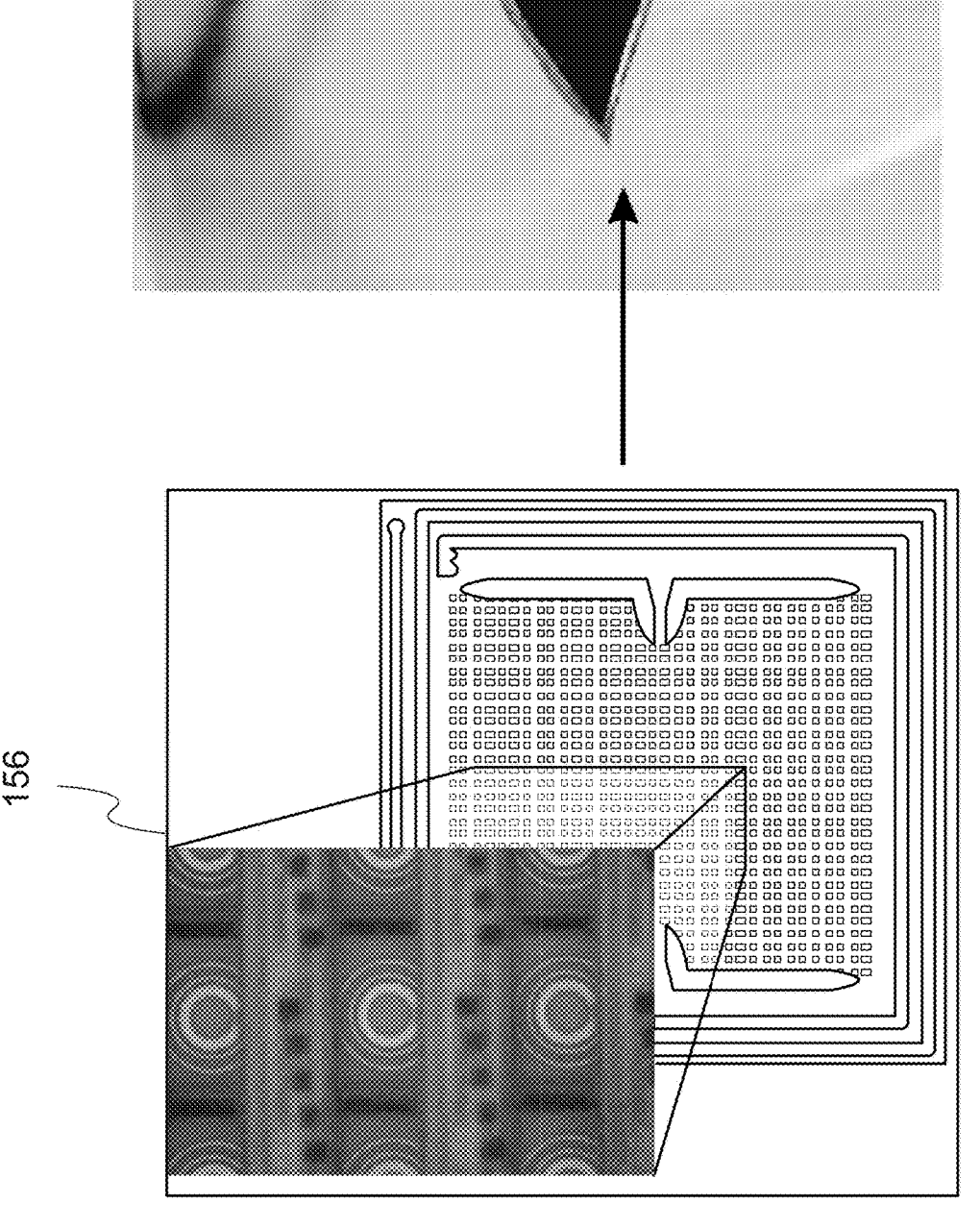
FIG. 1D is an exemplary fabrication procedure according to an exemplary of the present disclosure.

FIG. 1D illustrates an exemplary fabrication procedure according to an exemplary embodiment of the present disclosure. In particular, as shown in FIG. 1D, the implanted chip can be provided after undergoing the mechanical die-thinning and chemical encapsulation processes. This exemplary internal fabrication procedure can transform the standard stiff CMOS chips into the conformable platforms favorable for brain implants. In particular, the exemplary CMOS chip can be rendered flexible by extreme thinning of the integrated circuit. Specifically, the die-thinned chips can be bent to modest radiuses while maintaining the performance of the electronics. Bending stiffness for these dice scales roughly with the cube of the film thickness, facilitating a reduction in die bending stiffness from roughly 1.76 Nm for a standard 500 um thick die to only 5 uNm for a fully-thinned die. The resulting six-order-of-magnitude increase in mechanical compliance can facilitate the device to tightly conform to the curvilinear surface of the brain. Moreover, the full device can retain its flexibility due the PDMS-based imaging mask design and packaging. After thinning, e.g., a passivation layer that can include aluminium-oxide-parylene multilayers can be deposited to seal the device and make it biocompatible for implantation. This can reduce damage to the brain tissue as compared to other penetrating devices. Additionally, the imaging phase mask can be directly fabricated in a Polydimethylsiloxane ("PDMS")-based spacer with a 100 to 200 um thickness. Mechanical flexibility of PDMS makes the whole packaged device conformable to the surface of the brain. Image 168 illustrates the exemplary flexible device draped around a Beeker.

Figure 2:
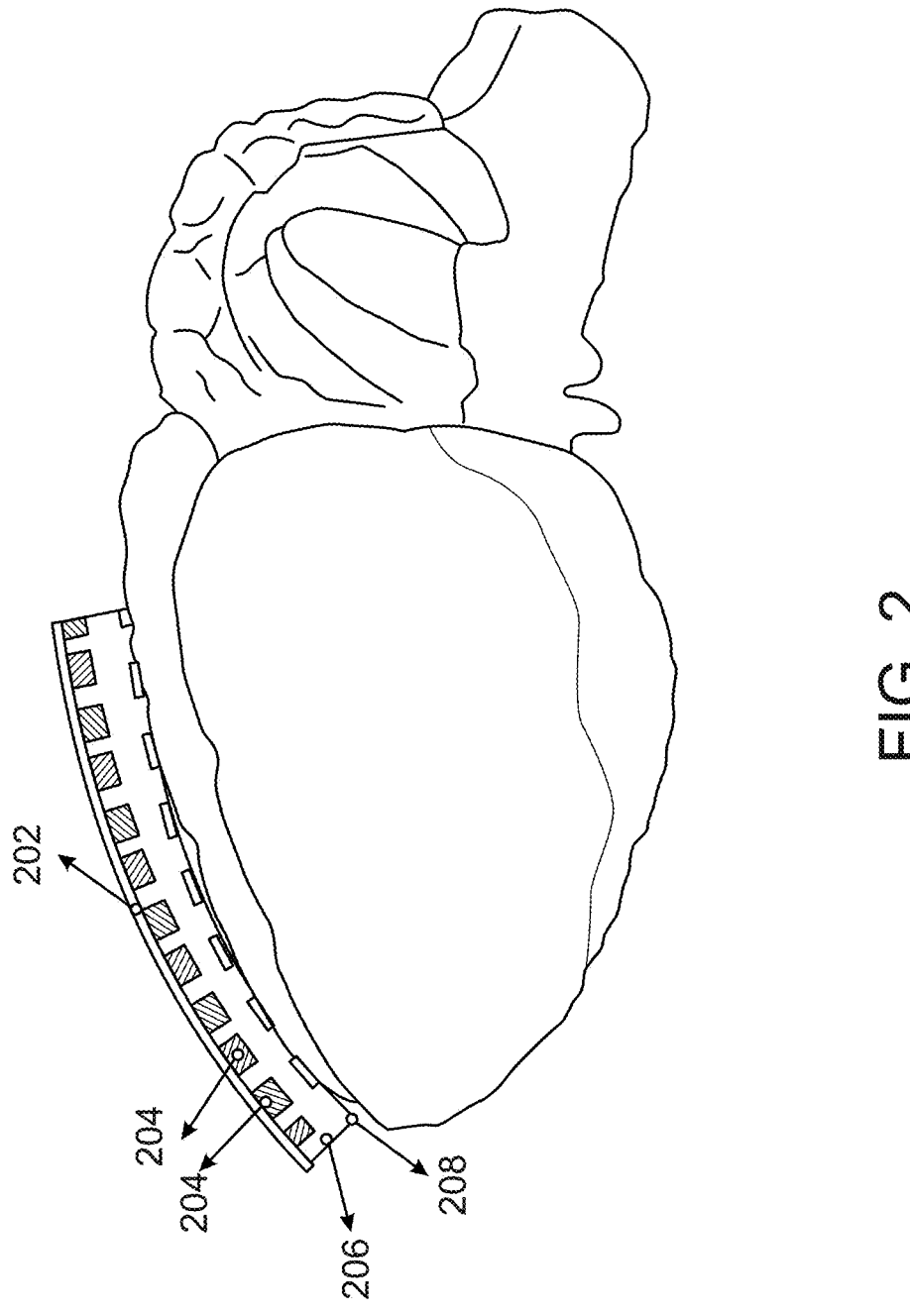
FIG. 2 is an exemplary packaging procedure for the exemplary apparatus according to an exemplary of the present disclosure.

FIG. 2 shows an exemplary packaging procedure for the exemplary apparatus according to an exemplary of the present disclosure. For example, by combining the exemplary integrated circuit design, nanotechnology, and imaging procedures, the exemplary apparatus can have a total thickness of 250 um. Further, arrays of micro-LEDs can be bonded as optogenetics and fluorescence excitation sources. Further, by exploiting the fast turn-off time, time-gated fluorescence imaging can be performed, thereby reducing or eliminating the need for optical filters. In addition, the use of relatively bulky conventional lenses can also be avoided or reduced by leveraging the use of computational imaging methods. As such, a relatively thin imaging mask (e.g., 100 to 200 um thick) can be utilized.

As shown in FIG. 2, an exemplary die-thinned flexible CMOS chip 202 can be inserted into or on the brain of a patient. CMOS chip 202 can include, e.g., a plurality of LED's 204 for imaging and optogenetics. A spacer layer 206, which can be about 100 μm thick (plus or minus about 10%), can separate LEDs 204 from Binary/phase mask 208, which can be used for computational imaging.

Figure 3:
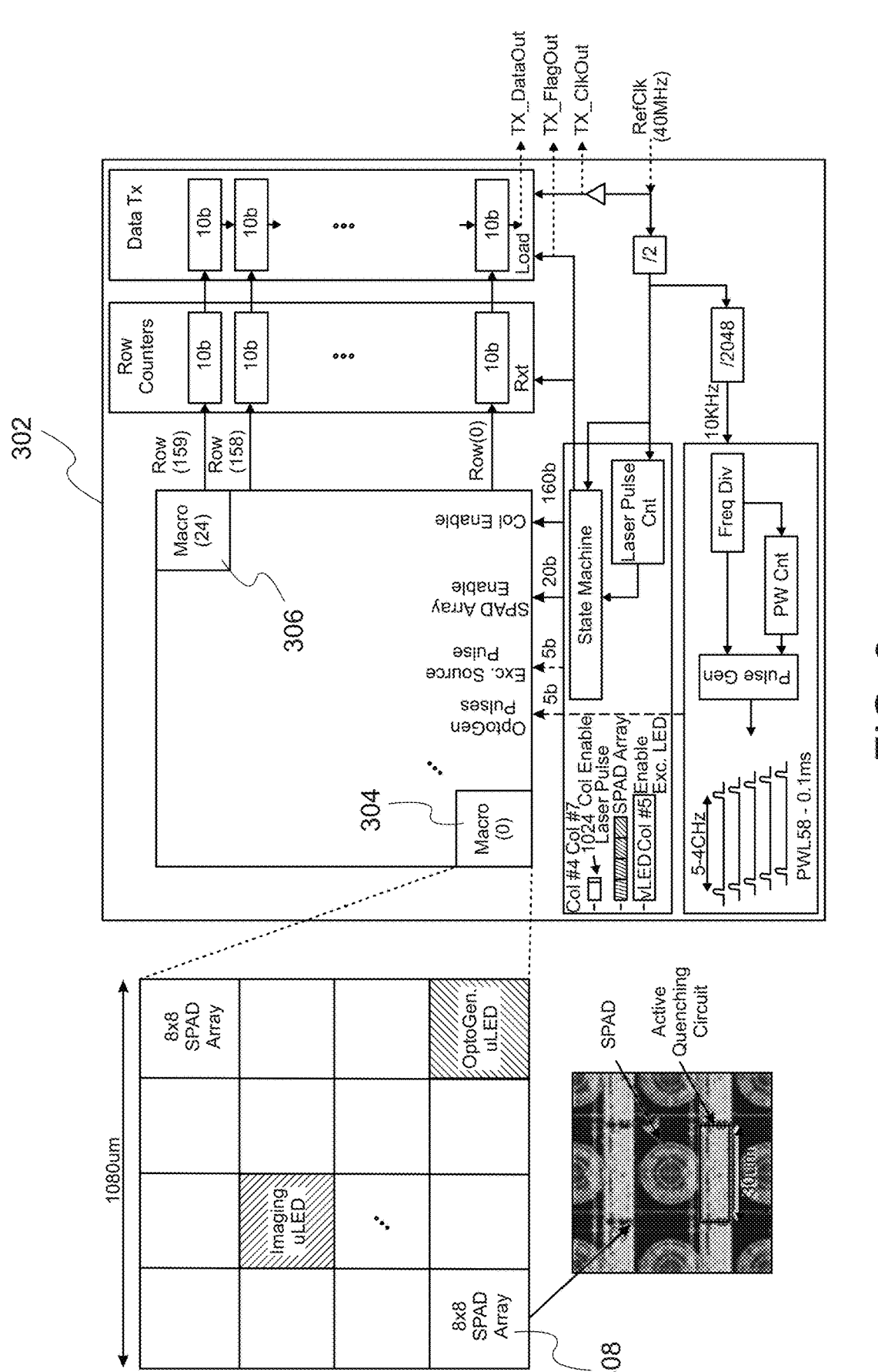
FIG. 3 is an exemplary block and schematic diagram of an exemplary integrated circuit chip according to an exemplary of the present disclosure.

FIG. 3 illustrates an exemplary block and schematic diagram of an exemplary integrated circuit chip 302 according to an exemplary embodiment of the present disclosure. The complete array can be split into 5×5 macros (e.g., Macro(0) shown by element 304 and Macro(24) shown by an element/component 306). Each imager pixel 308 can contain, e.g., a SPAD along with its AQC circuitry over a 30×30 um² area. Pixels can be activated in a rolling-shutter fashion for the duration of 1024 laser pulses. At the end of each column read, 10-bit counters for each row can be serialized through a shift-register and transferred to the wireless transceiver.

Figure 4:
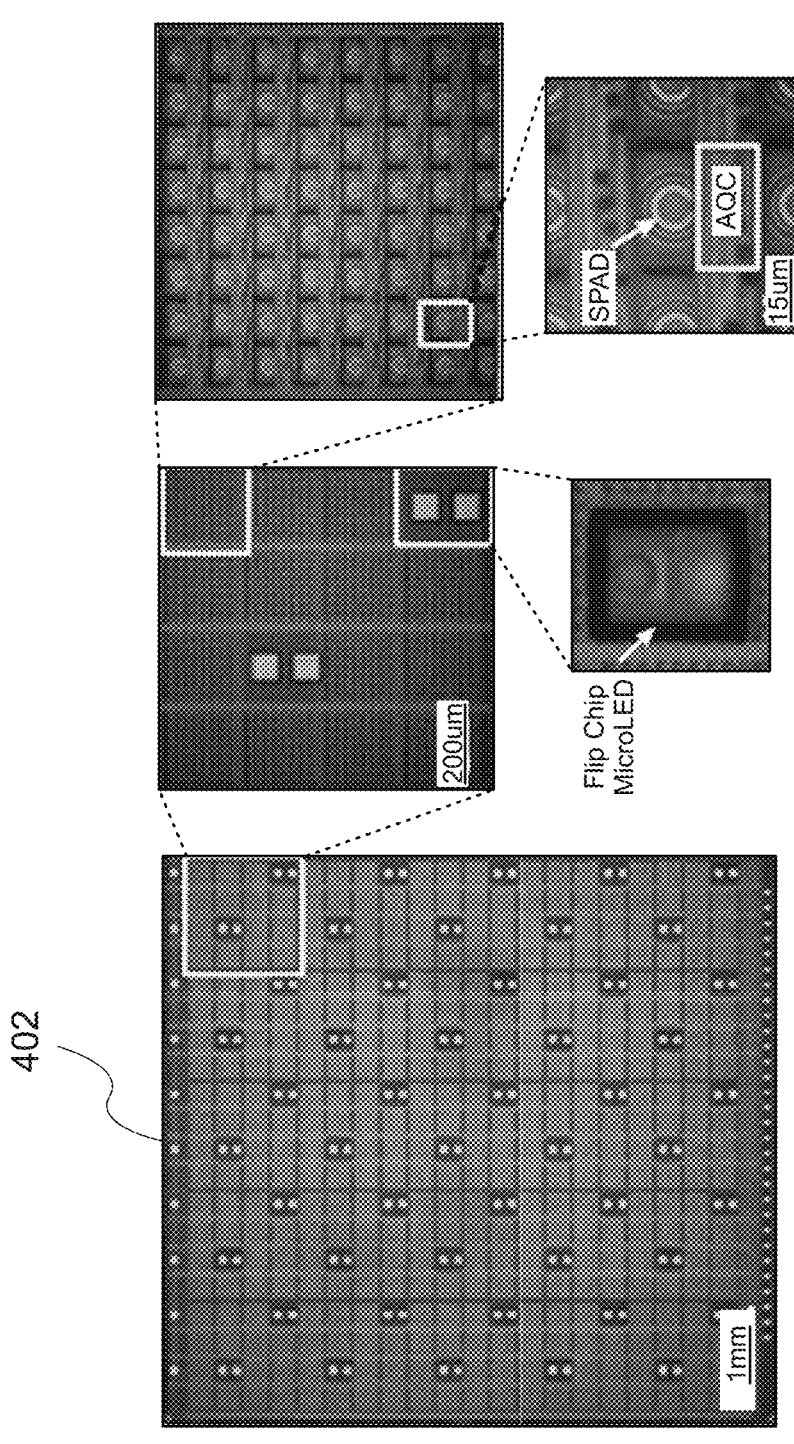
FIG. 4 are a set of exemplary micrographs of the exemplary integrated circuit chip shown in FIG. 3 according to an exemplary of the present disclosure.

FIG. 4 shows a set of exemplary micrographs 402 of the exemplary integrated circuit chip provided in FIG. 3 according to an exemplary embodiment of the present disclosure. In particular, FIG. 4 illustrates exemplary micrographs 402 of the wired versions of the exemplary integrated circuit chip. The total chip area can be, e.g., 6×6 mm², with the imaging and stimulation area of 5×5 mm² being comprised of 160×160 SPADs, 25 blue and 25 green micro-LEDs. Further, the depicted insets in FIG. 4 show that the unit cell of this array can contain flip-chip bonded micro-LEDs and monolithic SPAD arrays.

Figure 5:
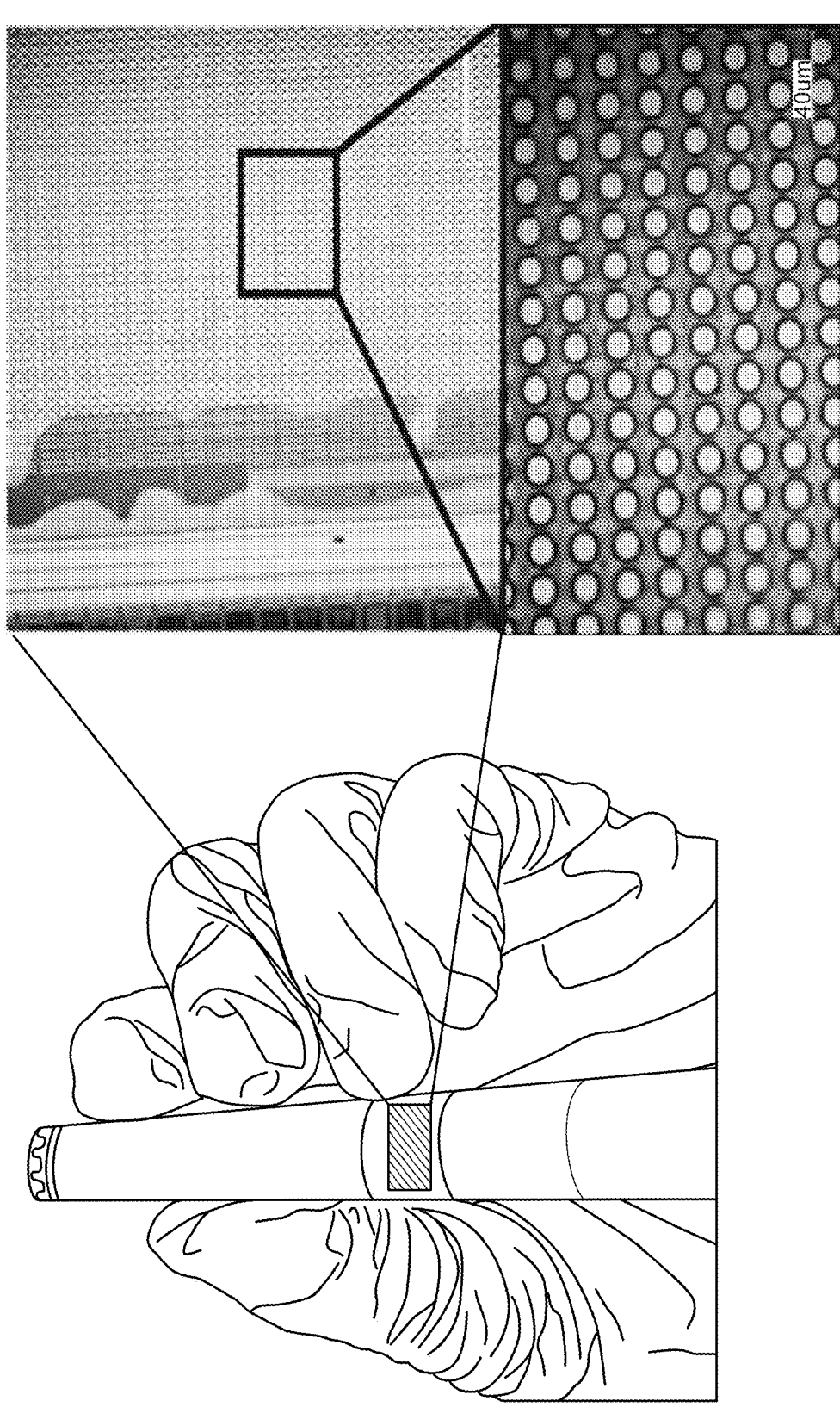
FIG. 5 are a set of exemplary photographs of a micro-electrode array according to an exemplary of the present disclosure.

FIG. 5 illustrates exemplary photographs of a microelectrode array according to an exemplary of the present disclosure. In particular, the photographs of FIG. 5 provide an ultra-thin functional microelectrode array, highlighting the extreme flexibility of these exemplary devices.

Figure 6:
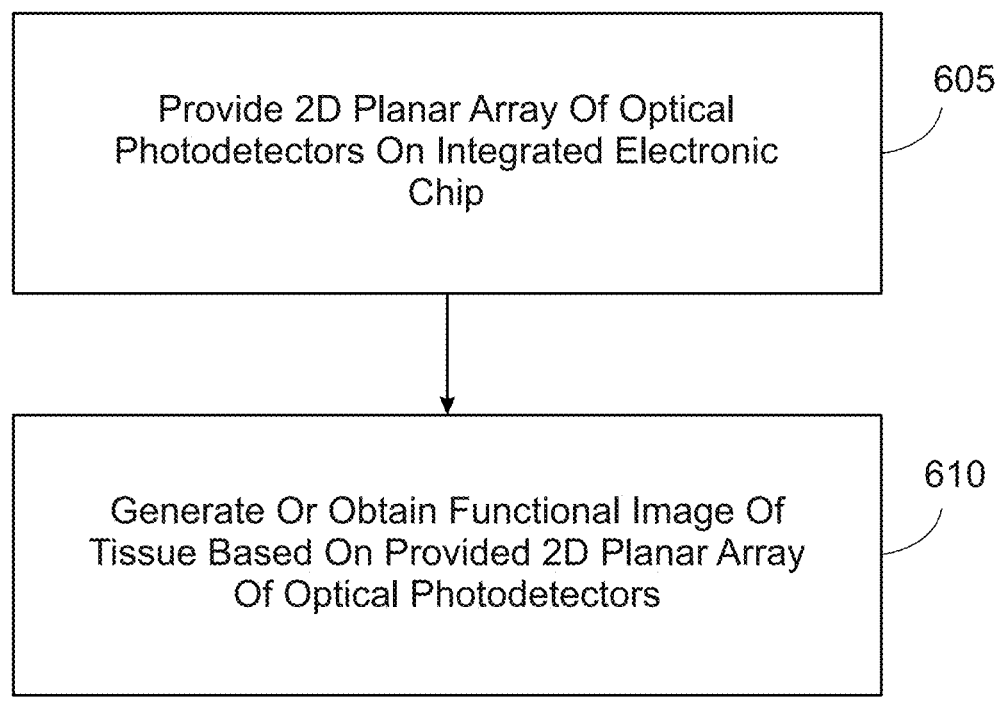
FIG. 6 is a flow diagram of an exemplary method for functional imaging of a tissue using a surgical implant according to an exemplary embodiment of the present disclosure.

FIG. 6 shows a flow diagram of an exemplary method 600 for functional imaging of a tissue using a surgical implant according to an exemplary embodiment of the present disclosure. For example, at procedure 605, a 2D planar array of optical photodetectors on an integrated electronic chip can be provided, where the integrated electronic chip can include control logic and image-capturing electronic circuitry, an amplitude or phase optical imaging mask for imaging, and a biocompatible packaging. At procedure 610, a functional image of the tissue can be generated or obtained based on the provided 2D planar array of optical photodetectors.

Figure 7:
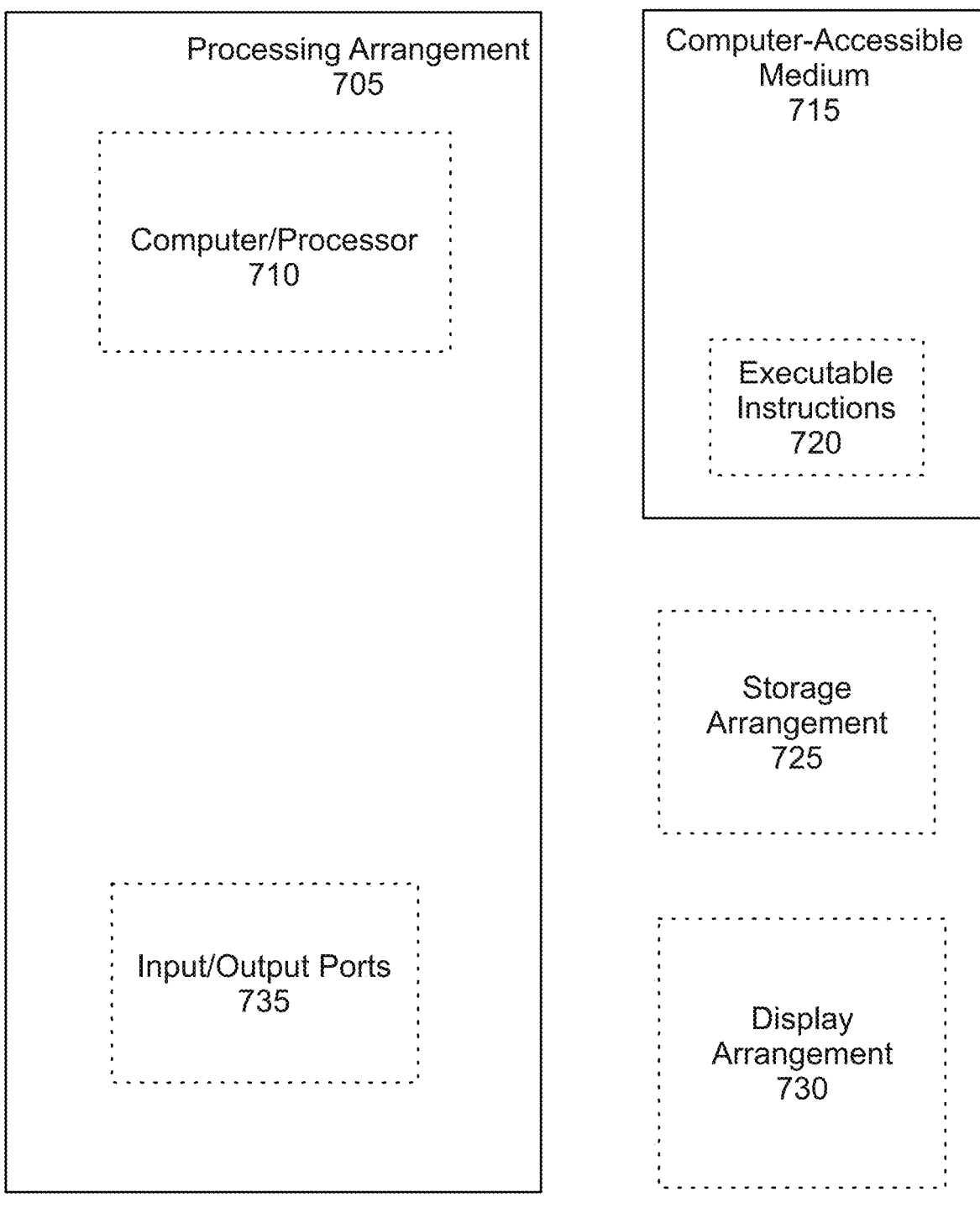
FIG. 7 is an exemplary block diagram of an exemplary system according to an exemplary of the present disclosure.

FIG. 7 shows a block diagram of an exemplary embodiment of a system according to the present disclosure. For example, exemplary procedures in accordance with the present disclosure described herein can be performed by a processing arrangement and/or a computing arrangement (e.g., computer hardware arrangement) 705. Such processing/computing arrangement 705 can be, for example entirely or a part of, or include, but not limited to, a computer/processor 710 that can include, for example one or more microprocessors, and use instructions stored on a computer-accessible medium (e.g., RAM, ROM, hard drive, or other storage device).

As illustrated in FIG. 7, for example a computer-accessible medium 715 (e.g., as described herein above, a storage device such as a hard disk, floppy disk, memory stick, CD-ROM, RAM, ROM, etc., or a collection thereof) can be provided (e.g., in communication with the processing arrangement 705). The computer-accessible medium 715 can contain executable instructions 720 thereon. In addition or alternatively, a storage arrangement 725 can be provided separately from the computer-accessible medium 715, which can provide the instructions to the processing arrangement 705 so as to configure the processing arrangement to execute certain exemplary procedures, processes, and methods, as described herein above, for example.

Further, the exemplary processing arrangement 705 can be provided with or include an input/output ports 735, which can include, for example a wired network, a wireless network, the internet, an intranet, a data collection probe, a sensor, etc. As shown in FIG. 7, the exemplary processing arrangement 705 can be in communication with an exemplary display arrangement 730, which, according to certain exemplary embodiments of the present disclosure, can be a touch-screen configured for inputting information to the processing arrangement in addition to outputting information from the processing arrangement, for example. Further, the exemplary display arrangement 730 and/or a storage arrangement 725 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification and drawings, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference in their entireties:

1. Emiliani, V., Cohen, A. E., Deisseroth, K., & Häusser, M. (2015). All-Optical Interrogation of Neural Circuits. *The Journal of Neuroscience,* 35(41), 13917 LP-13926.
2. Hochbaum, D. R., Zhao, Y., Farhi, S. L., Klapoetke, N., Werley, C. A., Kapoor, V., . . . Cohen, A. E. (2014). All-optical electrophysiology in mammalian neurons using engineered microbial rhodopsins. *Nature Methods,* 11, 825.
3. Zhang, Z., Russell, L. E., Packer, A. M., Gauld, O. M., & Häusser, M. (2018). Closed-loop all-optical interrogation of neural circuits in vivo. *Nature Methods,* 15(12), 1037-1040.
4. Ghosh, K. K., Burns, L. D., Cocker, E. D., Nimmerjahn, A., Ziv, Y., Gamal, A. El, & Schnitzer, M. J. (2011). Miniaturized integration of a fluorescence microscope. *Nature Methods,* 8, 871.
5. Scott, B. B., Thiberge, S. Y., Guo, C., Tervo, D. G. R., Brody, C. D., Karpova, A. Y., & Tank, D. W. (2018). Imaging Cortical Dynamics in GCaMP Transgenic Rats with a Head-Mounted Widefield Macroscope. *Neuron,* 100(5), 1045-1058. e5.
6. Stamatakis, A. M., Schachter, M. J., Gulati, S., Zitelli, K. T., Malanowski, S., Tajik, A., . . . Otte, S. L. (2018). Simultaneous Optogenetics and Cellular Resolution Calcium Imaging During Active Behavior Using a Miniaturized Microscope. *Frontiers in Neuroscience,* 12, 496.
7. Sawinski, J., Wallace, D. J., Greenberg, D. S., Grossmann, S., Denk, W., & Kerr, J. N. D. (2009). Visually evoked activity in cortical cells imaged in freely moving animals. *Proceedings of the National Academy of Sciences,* 106 (46), 19557 LP-19562.
8. Zong, W., Wu, R., Li, M., Hu, Y., Li, Y., Li, J., . . . Cheng, H. (2017). Fast high-resolution miniature two-photon microscopy for brain imaging in freely behaving mice. *Nature Methods,* 14, 713.
9. Lee, C., Taal, A. J., Choi, J., Kim, K., Tien, K., Moreaux, L., . . . Shepard, K. L. (2019). A 512-Pixel 3 kHz-Frame-Rate Dual-Shank Lensless Filterless Single-Photon-Avalanche-Diode CMOS Neural Imaging Probe. *IEEE International Solid-State Circuits Conference, ISSCC* 2019, *San Francisco, CA, USA, Feb.* 17-21, 2019, 198-200.
10. Rae, B. R., Muir, K. R., Gong, Z., McKendry, J., Girkin, J. M., Gu, E., . . . Henderson, R. K. (2009). A CMOS Time-Resolved Fluorescence Lifetime Analysis Micro-System. *Sensors,* 9(11), 9255-9274.
11. Adams, J. K., Boominathan, V., Avants, B. W., Vercosa, D. G., Ye, F., Baraniuk, R. G., . . . Veeraraghavan, A. (2017). Single-frame 3D fluorescence microscopy with ultraminiature lensless FlatScope. *Science Advances,* 3(12), e1701548.
12. Yona, G., Meitav, N., Kahn, I., & Shoham, S. (2016). Realistic Numerical and Analytical Modeling of Light Scattering in Brain Tissue for Optogenetic Applications. *ENeuro,* 3(1).
13. Gupta, S., Navaraj, W. T., Lorenzelli, L., & Dahiya, R. (2018). Ultra-thin chips for high-performance flexible electronics. *Npj Flexible Electronics,* 2(1), 8.
14. Kim, S., P. Tathireddy, R. A. Normann, and F. Solzbacher, *Thermal Impact of an Active* 3-D *Microelectrode Array Implanted in the Brain.* IEEE Transactions on Neural Systems and Rehabilitation Engineering, 2007. 15(4): p. 493-501.
Mirbozorgi, S. A., H. Bahrami, M. Sawan, L. A. Rusch, and B. Gosselin, *A Single-Chip Full-Duplex High Speed Transceiver for Multi-Site Stimulating and Recording Neural Implants.* IEEE Transactions on Biomedical Circuits and Systems, 2016. 10(3): p. 643-653.

What is claimed is:

1. A surgical implant for facilitating functional imaging of a tissue, comprising:
   an integrated electronic chip; and
   a 2-dimensional (2D) planar array of optical photodetectors provided on the integrated electronic chip, the integrated electronic chip including:
   i. control logic and image-capturing electronic circuitry,
   ii. at least one of an amplitude optical imaging mask or a phase optical imaging mask, and
   iii. a biocompatible packaging.

2. The surgical implant of claim 1, wherein the surgical implant is configured to functionally image the tissue that is nervous tissue or living brain tissue.

3. The surgical implant of claim 1, wherein the control logic and image-capturing electronic circuitry controls an imaging neuronal activity based on at least one optical reporter, and wherein the at least one optical reporter includes at least one of a genetically-encoded Calcium or voltage-dependent fluorescent protein, a bioluminescence protein, a chemical fluorescent reporter, or a fluorescent nanoparticle reporter.

4. The surgical implant of claim 1, wherein the imaging is lens-less and is based on computational imaging procedures.

5. The surgical implant of claim 1, wherein an imager surface is flexible and conformable to a tissue surface and curvature.

6. The surgical implant of claim 1, wherein the integrated electronic chip is a single complementary-metal-oxide-semiconductor (CMOS) chip.

7. The surgical implant of claim 1, wherein the integrated electronic chip is a single CMOS chip, which is die-thinned so as to be flexible and pliable.

8. The surgical implant of claim 1, wherein the biocompatible packaging includes a thickness of 500 micrometer or less.

9. The surgical implant of claim 1, wherein the surgical implant (i) is conformable to a tissue surface and curvature, and (ii) has a sticking structure that facilitates sticking to the tissue surface to minimize implant dislocations.

10. The surgical implant of claim 1, wherein the optical photodetectors are single-photon avalanche photodiodes (SPADs).

11. The surgical implant of claim 1, wherein an imaging field of view is about 0.25 cm$^2$ or larger.

12. The surgical implant of claim 1, wherein the surgical implant includes a weight of less than 5 grams.

13. The surgical implant of claim 4, wherein the control logic and image-capturing electronic circuitry controls imaging of 3D volumes using computational imaging procedures.

14. The surgical implant of claim 10, wherein the SPADs are time-gated.

15. The surgical implant of claim 1, further comprising light emitting diodes (LEDs) for fluorescence excitation of the tissue.

16. The surgical implant of claim 1, wherein a set of light emitting diodes (LEDs) are configured to optogenetically stimulate cortical regions in a brain.

17. The surgical implant of claim 16, wherein the surgical implant is configured to be used on the tissue having cells that are labeled with cell-specific Opsins to facilitate an optogenetics stimulation.

18. The surgical implant of claim 16, wherein the control logic and image-capturing electronic circuitry controls the LEDs provided in a 2D array to perform the optogenetics stimulation with a spatial selectivity and programmable patterns.

19. The surgical implant of claim 1, wherein the control logic and image-capturing electronic circuitry controls a wireless transmission of at least one of (i) electrical power and (ii) data in and out of the implant to an external relay station.

20. A method for facilitating functional imaging of a tissue using a surgical implant, comprising:

providing a 2-dimensional (2D) planar array of optical photodetectors on an integrated electronic chip, the integrated electronic chip including:

i. control logic and image-capturing electronic circuitry, ii. at least one of an amplitude optical imaging mask or a phase optical imaging mask, and iii. a biocompatible packaging.

21. The method of claim 20, further comprising generating or obtaining at least one functional image of the tissue using the provided 2D planar array of optical photodetectors.

* * * * *